US008653439B2

(12) United States Patent
Nauka et al.

(10) Patent No.: US 8,653,439 B2
(45) Date of Patent: Feb. 18, 2014

(54) IMAGE FORMING APPARATUS HAVING OPTICAL SENSOR SYSTEM, OPTICAL SENSOR SYSTEM HAVING HEATING MODULE FOR REMOVING DEPOSIT FORMATION OF VOLATILE ORGANIC COMPOUNDS THERE FROM, AND METHOD THEREOF (75) Inventors: Krzysztof Nauka, Palo Alto, CA (US); Seongsik Chang, Santa Clara, CA (US); Henryk Birecki, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 265 days.

(21) Appl. No.: 13/238,001

(22) Filed: Sep. 21, 2011

(65) Prior Publication Data
US 2013/0070231 A1    Mar. 21, 2013

(51) Int. Cl.
*H01J 40/14*    (2006.01)
(52) U.S. Cl.
USPC ..................................... 250/238; 250/227.25
(58) Field of Classification Search
USPC .............. 250/238, 239, 227.25, 221, 214.1, 250/222.2, 559.4; 340/602–604; 356/436–438
See application file for complete search history.

(56) References Cited

U.S. PATENT DOCUMENTS

| 5,790,246 | A | 8/1998 | Kuhnell et al. |
| 7,708,947 | B2 | 5/2010 | West et al. |
| 7,804,080 | B2 * | 9/2010 | Choi .............................. 250/573 |
| 7,924,412 | B2 | 4/2011 | Chopra et al. |
| 7,972,865 | B2 | 7/2011 | Yi et al. |
| 2010/0110437 | A1 | 5/2010 | Furtaw et al. |
| 2011/0048106 | A1 | 3/2011 | Zawacki et al. |

OTHER PUBLICATIONS

"What Precautions Should I Take When Using the Hobo Pro Data Loggers Outside?", <http://www.onsetcomp.com/support/faq/what-precautions-should-i-take-when-using-hobo-pro-loggers-outside >, 2011.
Stewart, K.M.E; "Doped Polyaniline for Gas Sensors for the Detection of Formaldehyde", <http://uwspace.uwaterloo.ca/bitstream/10012/5852/1/Stewart_Katherine.pdf >, 2011.
Stockdale, Mark; "Minipid User Manual V1.8", <http://www.ionscience.com/assets/files/manuals/MiniPID%20Manual%203%20Pin%20V1.8.pdf >, Aug. 11, 2010.

* cited by examiner

*Primary Examiner* — Que T Le (57) ABSTRACT

An optical sensor system is disclosed including a source module, a detection module, and a heating module. The source module includes a source housing unit having a source window member to emit a detection signal through the source window member. The detection module includes a first detection housing unit having a first detection window member spaced apart from the source module. The detection signal received by the detection module corresponds to an amount of volatile organic compounds (VOC) present in a path of the detection signal between the detection module and the source module. The heating module heats the source window member and the detection window member to remove deposit formation of the VOC there from.

20 Claims, 5 Drawing Sheets

IMAGE FORMING APPARATUS HAVING OPTICAL SENSOR SYSTEM, OPTICAL SENSOR SYSTEM HAVING HEATING MODULE FOR REMOVING DEPOSIT FORMATION OF VOLATILE ORGANIC COMPOUNDS THERE FROM, AND METHOD THEREOF

CROSS REFERENCE TO RELATED APPLICATIONS

This application is related to commonly-owned patent application Ser. No. 13/238,281, entitled "IMAGE FORMING APPARATUS HAVING OPTICAL SENSOR SYSTEM, OPTICAL SENSOR SYSTEM HAVING SHIELDS, AND METHOD THEREOF" and filed contemporaneously herewith by Seongsik Chang, Henryk Birecki, and Krzysztof Nauka, and, Ser. No. 13/238,015 entitled "IMAGE FORMING APPARATUS HAVING OPTICAL SENSOR SYSTEM, OPTICAL SENSOR SYSTEM HAVING DETECTION MODULES, AND METHOD THEREOF" and filed contemporaneously herewith by Henryk Birecki, Krzysztof Nauka, and Seongsik Chang, and which related applications are incorporated herein by reference in their entirety.

BACKGROUND

Optical sensor systems may include source modules and detection modules to detect the presence of objects there between. The source modules and detection modules may include respective window members. The source module may emit a detection signal such as an infrared signal to pass through the respective window members and be received by the detection module. The objects such as volatile organic compounds (VOC) may be detected in a path of the detection signal. Such optical sensor systems may be included in image forming apparatuses, air quality monitoring devices, or the like.

BRIEF DESCRIPTION OF THE DRAWINGS

Non-limiting examples of the present disclosure are described in the following description, read with reference to the figures attached hereto and do not limit the scope of the claims. In the figures, identical and similar structures, elements or parts thereof that appear in more than one figure are generally labeled with the same or similar references in the figures in which they appear. Dimensions of components and features illustrated in the figures are chosen primarily for convenience and clarity of presentation and are not necessarily to scale. Referring to the attached figures:

DETAILED DESCRIPTION

In the following detailed description, reference is made to the accompanying drawings which form a part hereof, and in which is depicted by way of illustration specific examples in which the present disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims.

Optical sensor systems may include source modules and detection modules to detect the presence of objects there between such as volatile organic compounds (VOC). For example, VOC may be in a form of a gas, liquid and/or solid and include organic compounds that may easily become vapor or gaseous. An optical sensor system may detect VOC in a form of a gas in a volume of air between a source module and a detection module, for example, to be used as a basis for determining a total amount of VOC in a form of a gas present in an environment. Such information may be used to provide alerts based on VOC concentration and/or activate processes to reduce VOC concentration. The source modules may include a source window member and emit a detection signal such as an infrared signal that passes through it to be received by a detection module through a detection window member thereof. The objects, for example, such as VOC may be detected when present in the path of the detection signal between the source module and detection module. Such optical sensor systems may be included in image forming apparatuses, air quality monitoring devices, or the like. The Image forming apparatuses may include liquid electrophotography printing apparatuses to form images on an image transfer blanket that, subsequently, get transferred to media. Unwanted deposits in a form of solid and/or liquid buildup such as VOC deposits, however, may form on the source window member and the detection window member. The deposits may decrease transmission of the detection signal through the respective window members, for example, by absorbing some frequencies of the detection signal and/or promoting scattering due to non-uniformity of the thickness of the deposits. Consequently, the detection signal may be degraded and/or potentially distort detection of objects such as the VOC in the form of a gas present in its path.

In examples, an optical sensor system includes, amongst other things, a source module, a detection module, and a heating module. The source module includes a source housing unit having a source window member to emit a detection signal through the source window member. The detection module includes a detection housing unit having a detection window member spaced apart from the source module. The detection signal received by the detection module may correspond to an amount of the VOC present in a path of the detection signal between the detection module and the source module. For example, deposit formation of the VOC on respective window members may contribute to a change in the detection signal emitted from the source module. The heating module may heat the source window member and the detection window member to remove deposit formation of VOC there from, for example, by volatilizing them. Thus, degradation of the detection signal and/or potentially distortion of the detection of objects such as the VOC in the form of a gas present in the path of the detection signal due to deposit formation on respective window members may be reduced. Additionally, in some examples, an image forming apparatus including an optical sensor system may heat the respective window members with the image forming apparatus—in-situ and without removing the optical sensor system and/or portions thereof from the image forming apparatus.

Figure 1:
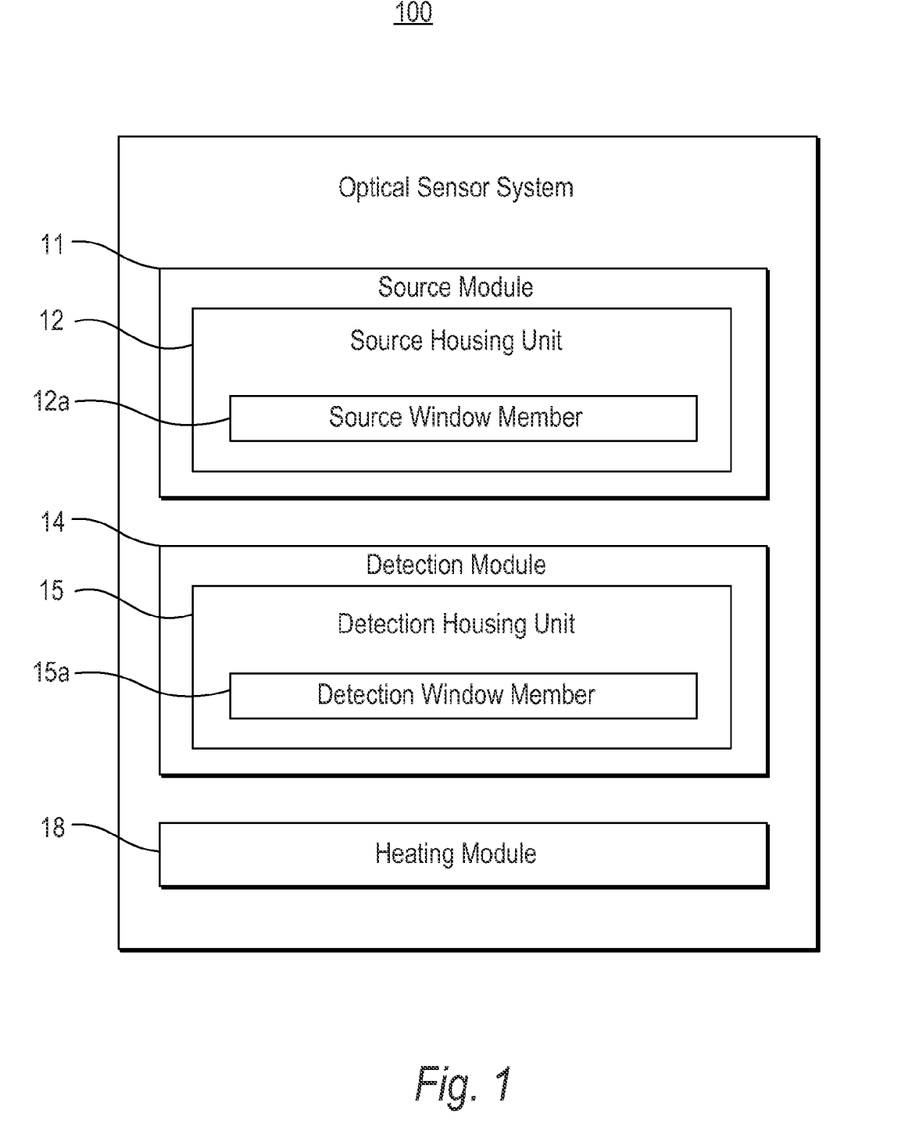
FIG. 1 is a block diagram illustrating an optical sensor system according to an example.

FIG. 1 is a block diagram illustrating an optical sensor system apparatus according to an example. Referring to FIG. 1, in some examples, an optical sensor system 100 includes a source module 11, a detection module 14 and a heating module 18. The source module 11 includes a source housing unit 12 having a source window member 12a. The source module 11 may emit a detection signal through the source window member 12a. The detection module 14 includes a detection housing unit 15 having a detection window member 15a. The detection module 14 is spaced apart from the source module 11 to detect the detection signal emitted from the source module 11 at the detection window member 15a. The heating module 18 may heat the source window member 12a and the detection window member 15a to remove deposit formation of VOC there from. That is, the heated source window member 12a and the heated detection window member 15a may vaporize and/or reduce deposit formation of the VOC on the source window member 12a and the detection window member 15a. In some examples, the heating module 18 may include a single heating unit to heat both the source window member 12a and the detection window member 15a. Alternatively, in some examples, the heating module 18 may include at least one heating unit to heat the source window member 12a and at least another heating unit to heat the detection window member 15a. The detection signal received by the detection module 14 may correspond to the amount of the VOC 22 (FIG. 2) present in the path of the detection signal between the detection module 14 and the source module 11.

Figure 2:
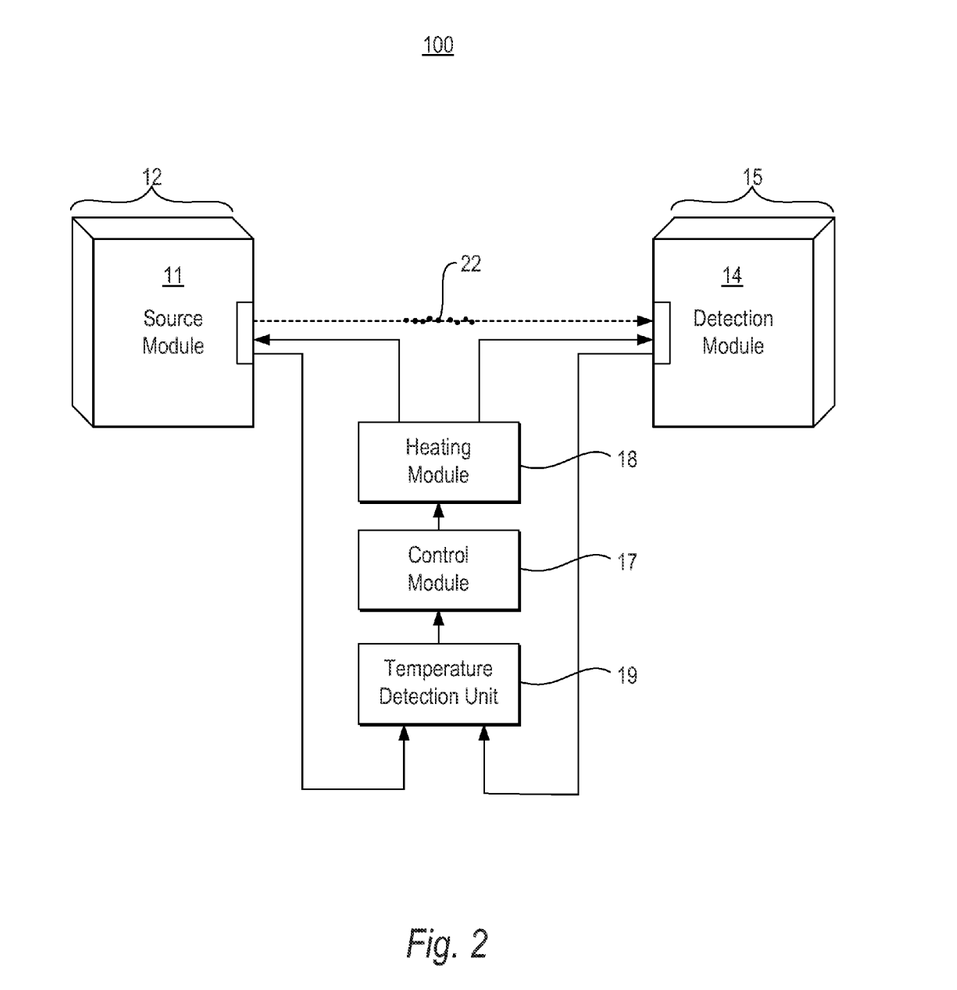
FIG. 2 is a schematic diagram of the optical sensor system of FIG. 1 according to an example.

FIG. 2 is a schematic view illustrating the optical sensor system of FIG. 1 according to an example. Referring to FIG. 2, in some examples, the optical sensor system 100 may also include a temperature detection unit 19 and a control module 17. The temperature detection unit 19 may detect a respective temperature of the source window member 12a and the detection window member 15a. In some examples, the control module 17 may control the heating module 18 by at least one of selectively activating the heating module 18, selectively deactivating the heating module 18, selectively communicating to the heating module 18 to increase the respective temperature of at least one of the source window member 12a and the detection window member 15a, and selectively communicating to the heating module 18 to decrease the respective temperature of at least one of the source window member 12a and the detection window member 15a.

In some examples, the control module 17 may intermittently activate the heating module 18 to heat the source window member 12a and the detection window member 15a to a respective temperature in a range of 140 degrees Celsius to 190 degrees Celsius. The control module 17 may control the heating module 18 based on the temperature values by the temperature detection unit 19. For example, the temperature detection unit 19 may include a source window temperature sensor proximate to the source window member 12a to measure a temperature of the source window member 12a and a detection window temperature sensor proximate to the detection window member 15a to measure a temperature of the detection window member 12a. In some examples, the control module 17 may control the heating module 18 based on a determination of an amount of deposit formation of the VOC on the source window member 12a and the detection window member 15a.

In some examples, the control module 17 may selectively activate and deactivate the heating module 18 for a predetermined period of time. For example, the predetermined period of time may correspond to an amount of time to maintain the respective window members 12a and 15a in a predetermined temperature range. In some examples, the control module 17 may deactivate the heating module 18 during VOC detection and activate the heating module 18 during periods without VOC detection, activate the heating module 18 to heat the respective window members 12a and 15a during the detection of the amount of VOC in the path of the detection signal, activate the heating module 18 periodically as deemed necessary, or the like. In some examples, the heating may be realized by a constant amplitude signal or pulses.

Figure 3A:
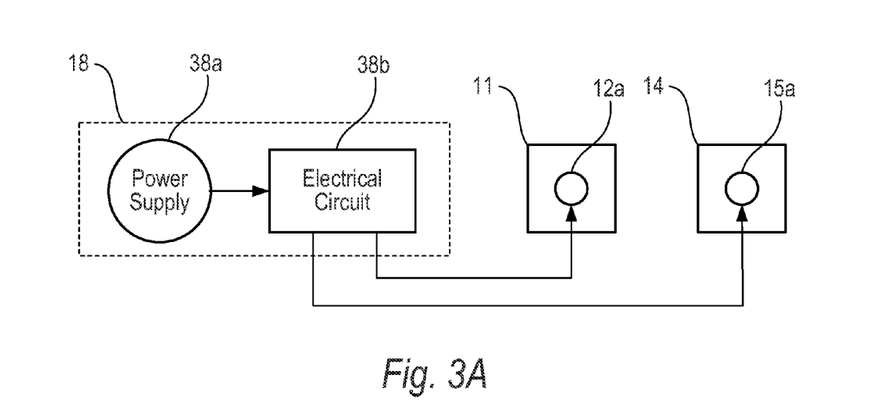
FIG. 3A is a schematic view illustrating a heating module coupled to a source window member and a detection window member of the optical sensor system of FIG. 1 according to an example.
Figure 3B:
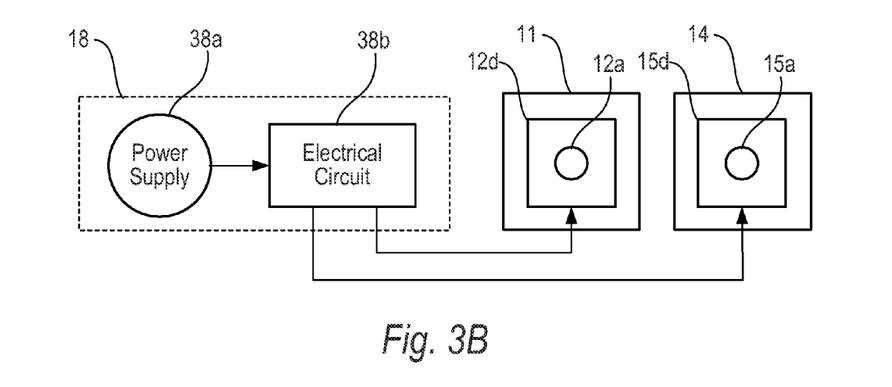
FIG. 3B is a schematic view illustrating a heating module coupled to a source window mounting member and a detection window mounting member of the optical sensor system of FIG. 1 according to an example.
Figure 3C:
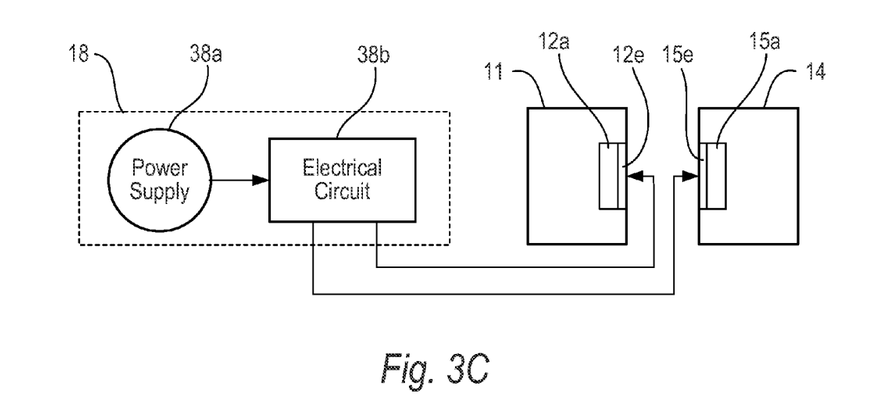
FIG. 3C is a schematic view illustrating a heating module coupled to a source screening member and a detection screening member of the optical sensor system of FIG. 1 according to an example.

FIG. 3A is a schematic view of a heating module coupled to a source window member and a detection window member of the optical sensor system of FIG. 1 according to an example. FIG. 3B is a schematic view of a heating module coupled to a source window mounting member and a detection window mounting member of the optical sensor system of FIG. 1 according to an example. FIG. 3C is a schematic view of a heating module coupled to a source screening member and a detection screening member of the optical sensor system of FIG. 1 according to an example. Referring to FIGS. 3A-3C, in some examples, the heating module may 18 include a power source 38a and an electrical circuit 38b disposed between the power source 38a, the source window member 12a and the detection window member 15a. The electrical circuit 38b may provide an electrical current to heat the source window member 12a and the detection window member 15a. For example, the source window member 12a and the detection window member 15a may include an electrically conductive material having an amount of transparency to infrared. For example, the respective window members 12a and 15a may include silicon, germanium, or the like, having an amount of electrical resistivity capable of providing its resistive heating as electrical current passes through it. The electrical circuit 38b may be coupled to and directly apply an electrical current to the source window member 12a and the detection window member 15a to provide heat thereto as illustrated in FIG. 3A.

Referring to FIG. 3B, in some examples, the source housing unit 12 may also include an electrically conductive source window mounting member 12d having an amount of electrical resistivity capable of providing its resistive heating as electrical current passes through it, and holding the source window member 12a to apply heat thereto. Additionally, the detection housing unit 15 may also include an electrically conductive detection window mounting member 15d having an amount of electrical resistivity capable of providing its resistive heating as electrical current passes through it, and holding the detection window member 15a to apply heat thereto. In such a case, the source window member 12a and detection window member 15a may be electrically nonconductive. The electrical circuit 38b may provide an electrical current to heat the source window mounting member 12d and the detection window mounting member 15d. For example, the electrical circuit 38b may be coupled to and directly apply an electrical current to the source window mounting member 12d and the detection window mounting member 15d to provide heat thereto as illustrated in FIG. 3B. Accordingly, the heated source window mounting member 12d may provide heat to the source window member 12a and the heated detection mounting member 15d may provide heat to the detection window member 15a. Alternatively, in some examples, the heating of the respective mounting members 12d and 15d may include providing a flow of hot fluid therein, generating an AC current therein, or the like.

Referring to FIG. 3C, in some examples, the source module 11 may also include an electrically conductive source window screening member 12e having an amount of transparency to infrared to contact and cover the source window member 12a. In such a case, the source window member 12a may be electrically nonconductive. The detection module 14 may also include an electrically conductive detection window screening member 15e having an amount of transparency to infrared to contact and cover the detection window member 15a. For example, the source and detection window screening members 12e and 15e may include a thin layer of electrically conductive silicon, a thin layer of electrically conductive germanium, a network of carbon nanofibers, a metallic mesh with sufficient wire spacing to allow light transmission there through, or the like. In such a case, the detection window member 15a may be electrically nonconductive.

Referring to FIG. 3C, in some examples, the heating module 18 may heat the electrically conductive source window screening member 12e which, in turn, heats the source window member 12a. The heating module 18 may heat the electrically conductive detection window screening member 15e which, in turn, heats the detection window member 15a. That is, the heat from the respective window screening members 12e and 15e may transfer heat to the corresponding window members 12a and 15a. For example, the electrical circuit 38b may be coupled to and directly apply an electrical current to the source window screening member 12e and the detection window screening member 15e to provide heat thereto as illustrated in FIG. 3C.

In some examples, the source module 11 may heat the source window member 12a in one of a direct manner, an indirect manner through a source window mounting member 12d, or an indirect manner through a source window screening member 12e, while the detection module 14 may heat the detection window member 15a in another one of a direct manner, an indirect manner through a source window mounting member 12d, or an indirect manner through a source window screening member 12e. For example, the source window member 12a may be heated indirectly through the source window mounting member 12d while the detection window member 15a may be heated directly by providing an electrical current directly through the detection window member 15a. In some examples, the respective window members 12a and 15a, the respective window mounting members 12d and 15d, and/or the respective window screening members 12e and 15e may be mostly transparent in an IR wavelength range from 3.3 microns to 3.0 microns.

In some examples, the source module 11, the detection module 14, the heating module 18, the temperature detection unit 19 and/or the control module 17 may be implemented in hardware, or in a combination of hardware and software. In some examples, the source module 11, the detection module 14, the heating module 18, the temperature detection unit 19 and/or the control module 17 may be implemented in part as a computer program such as a set of machine-readable instructions stored in the optical sensor system 100 locally or remotely. For example, the computer program may be stored in a memory such as a server or a host computing device considered herein as part of the optical sensor system 100.

Figure 4:
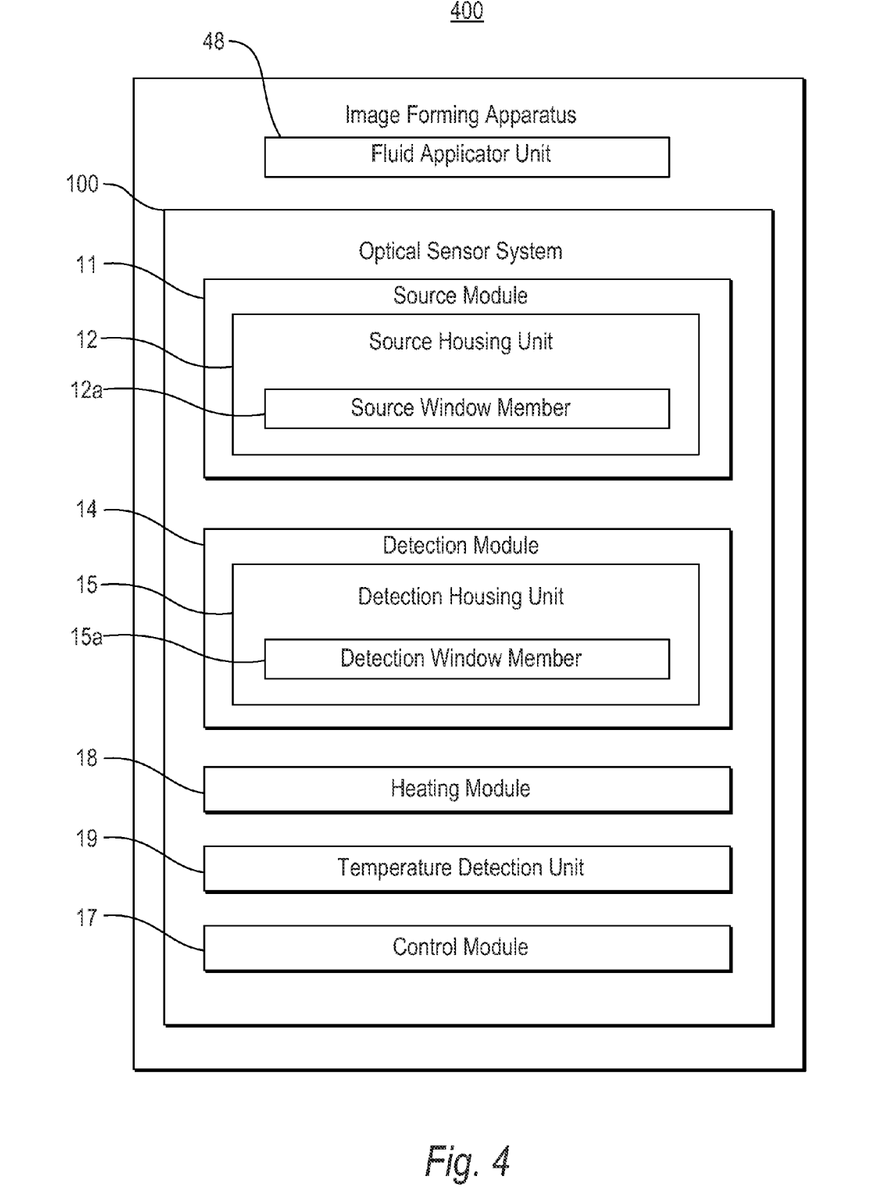
FIG. 4 is a block diagram illustrating an image forming apparatus having an optical sensor system according to an example.

FIG. 4 is a block diagram illustrating an image forming apparatus including an optical sensor system according to an example. In some examples, the image forming apparatus 400 may include a liquid electrophotography printing apparatus that forms images on media by applying fluid onto an image transfer blanket of an intermediate member and, subsequently, onto the media. For example, the fluid may include ink such as liquid toner, for example, Electrolnk, trademarked by Hewlett-Packard Company including imaging oil, for example, Isopar, trademarked by Exxon Corporation. Referring to FIG. 4, in some examples, an image forming apparatus 400 includes a fluid applicator unit 48 and an optical sensor system 100. The fluid applicator unit 48 may apply fluid to an object such as an image transfer blanket or a media to form an image. For example, the fluid applicator unit 48 may include an inkjet print head, a binary developer unit, or the like.

Referring to FIG. 4, in some examples, the optical sensor system 100 may detect VOC formed from the fluid applied by the fluid applicator unit 48. The optical sensor system 100 may include a source module 11, a detection module 14 spaced apart from each other, a heating module 18, a temperature detection unit 19, and a control module 17 as previously disclosed with respect to FIGS. 2-3C. For example, the source module 11 may include a source housing unit 12 having a source window member 12a. The source module 11 may emit a detection signal through the source window member 12a to detect the VOC present in a path of the detection signal between the source module 11 and the detection module 14. For example, the detection module 14 may include a detection housing unit 15 having a detection window member 15a to receive the detection signal emitted from the source module 11. The heating module 18 may heat the source window member 15a and the detection window member 15a to remove deposit formation of the VOC there from. The temperature detection unit 19 may detect a respective temperature of the source window member 12a and the detection window member 15a. The control module 17 may control the heating module 18 based on a detection by the temperature detection unit 19.

Figure 5:
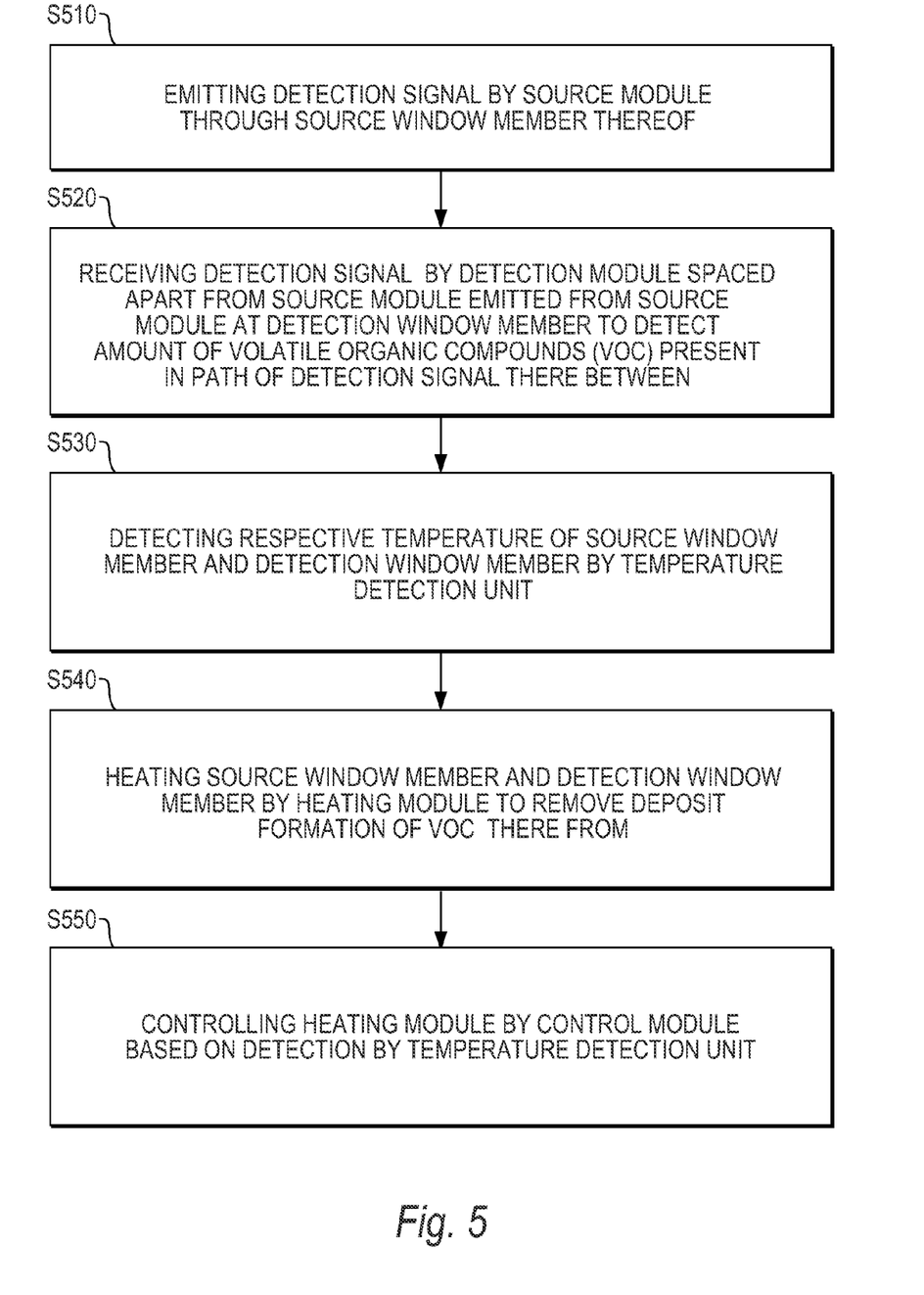
FIG. 5 is a flowchart of a method to detect volatile organic compounds according to an example.

FIG. 5 is a flowchart illustrating a method to detect volatile organic compounds according to an example. Referring to FIG. 5, in block 510, a detection signal is emitted by a source module through a source window member thereof. In block S520, the detection signal is received by a detection module spaced apart from the source module emitted from the source module at the detection window member to detect an amount of VOC present in a path of the detection signal between the source module window and detector module window. In block S530, a respective temperature of the source window member and the detection window member is detected by a temperature detection unit. In block S540, the source window member and the detection window member are heated by a heating module to remove deposit formation of the VOC there from.

In some examples, the heating the source window member and the detection window member by a heating module may also include providing an electrical current to the electrically conductive source window member and the electrically conductive detection window member in which electrical resistivity of both window members are selected to achieve the desired temperature. Alternatively, the heating the source window member and the detection window member by a heating module may also include providing an electrical current to an electrically conductive source mounting member holding the source window member and an electrically conductive detection mounting member holding the detection window member. In some examples, the heating of the respective mounting members may also include providing a flow of a hot fluid therein, generating an AC current therein, or the like. Yet still, the heating the source window member and the detection window member by a heating module may also include providing an electrical current to an electrically conductive source screening member having an amount of transparency to infrared in contact with and covering, for example, the electrically non-conductive source window member and an electrically conductive detection screening member having an amount of transparency to infrared in contact with and covering the electrically non-conductive detection window member. In block S550, the heating module is controlled by a control module based on the detection by the temperature detection unit.

It is to be understood that the flowchart of FIG. 5 illustrates an architecture, functionality, and operation of an example of the present disclosure. If embodied in software, each block may represent a module, segment, or portion of code that includes one or more executable instructions to implement the specified logical function(s). If embodied in hardware, each block may represent a circuit or a number of interconnected circuits to implement the specified logical function(s). Although the flowchart of FIG. 5 illustrates a specific order of execution, the order of execution may differ from that which is depicted. For example, the order of execution of two or more blocks may be scrambled relative to the order illustrated. Also, two or more blocks illustrated in succession in FIG. 5 may be executed concurrently or with partial concurrence. All such variations are within the scope of the present disclosure.

The present disclosure has been described using non-limiting detailed descriptions of examples thereof and is not intended to limit the scope of the present disclosure. It should be understood that features and/or operations described with respect to one example may be used with other examples and that not all examples of the present disclosure have all of the features and/or operations illustrated in a particular figure or described with respect to one of the examples. Variations of examples described will occur to persons of the art. Furthermore, the terms "comprise," "include," "have" and their conjugates, shall mean, when used in the present disclosure and/or claims, "including but not necessarily limited to."

It is noted that some of the above described examples may include structure, acts or details of structures and acts that may not be essential to the present disclosure and are intended to be exemplary. Structure and acts described herein are replaceable by equivalents, which perform the same function, even if the structure or acts are different, as known in the art. Therefore, the scope of the present disclosure is limited only by the elements and limitations as used in the claims.

What is claimed is:

1. An optical sensor system, comprising:
   a source module including a source housing unit having a source window member, the source module to emit a detection signal through the source window member;
   a detection module including a detection housing unit having a detection window member, the detection module spaced apart from the source module to detect the detection signal emitted from the source module at the detection window member; and
   a heating module to heat the source window member and the detection window member to remove deposit formation of volatile organic compounds (VOC) there from; and
   wherein the detection signal received by the detection module corresponds to an amount of the VOC present in a path of the detection signal between the detection module and the source module.

2. The optical sensor system according to claim 1, further comprising:
   a control module to control the heating module by at least one of selectively activating the heating module, selectively deactivating the heating module, selectively communicating to the heating module to increase the respective temperature of at least one of the source window member and the detection window member, and selectively communicating to the heating module to decrease the respective temperature of at least one of the source window member and the detection window member.

3. The optical sensor system according to claim 2, further comprising:
   a temperature detection unit to detect a respective temperature of the source window member and the detection window member; and
   wherein the control module controls the heating module based on the detection by the temperature detection unit.

4. The optical sensor system according to claim 2, wherein the control module intermittently activates the heating module to heat the source window member and the detection window member to a respective temperature in a range of 140 degrees Celsius to 190 degrees Celsius.

5. The optical sensor system according to claim 3, wherein the temperature detection unit detects respective temperatures of the source window member and the detection window member by detecting respective amounts of resistance thereof and determining respective temperatures corresponding to the respective detected amounts of resistance detected.

6. The optical sensor system according to claim 1, wherein the source window member and the detection window member comprise an electrically conductive material having an amount of transparency to infrared.

7. The optical sensor system according to claim 1, wherein the source housing unit further comprises an electrically conductive source window mounting member to hold the source window member and the detection housing unit further comprises an electrically conductive detection window mounting member to hold the detection window member such that the heating module heats the electrically conductive source mounting member to heat the source window member and heats the electrically conductive detection mounting member to heat the detection window member.

8. The optical sensor system according to claim 1, wherein the source module further comprises an electrically conductive source window screening member having an amount of transparency to infrared to contact and cover the source window member and the detection module further comprises an electrically conductive detection window screening member having an amount of transparency to infrared to contact and cover the detection window member such that the heating module heats the electrically conductive source window screening member to heat the source window member and heats the electrically conductive detection window screening member to heat the detection window member.

9. The optical sensor system according to claim 1, wherein the heating module comprises:
   a power source; and
   an electrical circuit disposed between the power source, the source window member and the detection window member to provide an electrical current to heat the source window member and the detection window member.

10. An image forming apparatus, comprising:
    a fluid applicator unit to apply fluid to an object to form an image; and
    an optical sensor system to detect volatile organic compounds (VOC) formed from the fluid applied by the fluid applicator unit, the optical sensor system including:

a source module including a source housing unit having a source window member, the source module to emit a detection signal through the source window member;

a detection module including a detection housing unit having a detection window member, the detection module spaced apart from the source module to receive the detection signal emitted from the source module at the detection window member corresponding to an amount of the VOC present in a path of the detection signal there between;

a heating module to heat the source window member and the detection window member to remove deposit formation of the VOC there from;

a temperature detection unit to detect a respective temperature of the source window member and the detection window member; and a control module to control the heating module based on a detection by the temperature detection unit.

11. The image forming apparatus according to claim 10, wherein the control module controls the heating module by at least one of selectively activating the heating module, selectively deactivating the heating module, selectively communicating to the heating module to increase the respective temperature of at least one of the source window member and the detection window member, and selectively communicating to the heating module to decrease the respective temperature of at least one of the source window member and the detection window member.

12. The image forming apparatus according to claim 11, wherein the heating module heats the source window member and the detection window member to the respective temperature in a range of 140 degrees Celsius to 190 degrees Celsius.

13. The image forming apparatus according to claim 10, wherein the source window member and the detection window member comprise an electrically conductive material transparent to infrared.

14. The image forming apparatus according to claim 10, wherein the source housing unit further comprises an electrically conductive source window mounting member to hold the source window member and the detection housing unit further comprises an electrically conductive detection window mounting member to hold the detection window member such that the heating module heats the electrically conductive source mounting member to heat the source window member and heats the electrically conductive detection mounting member to heat the detection window member.

15. The image forming apparatus according to claim 10, wherein the source module further comprises an electrically conductive source window screening member having an amount of transparency to infrared to contact and cover the source window member and the detection module further comprises an electrically conductive detection window screening member having an amount of transparency to infrared to contact and cover the detection window member such that the heating module heats the source window screening member to heat the source window member and heats the detection window screening member to heat the detection window member.

16. The image forming apparatus according to claim 10, wherein the heating module comprises:

a power source; and an electrical circuit disposed between the power source, the source window member and the detection window member to provide an electrical current to heat the source window member and the detection window member.

17. A method to detect volatile organic compounds, the method comprising:

emitting a detection signal by a source module through a source window member thereof;

receiving the detection signal by a detection module spaced apart from the source module emitted from the source module at the detection window member to detect an amount of volatile organic compounds (VOC) present in a path of the detection signal there between;

detecting a respective temperature of the source window member and the detection window member by a temperature detection unit;

heating the source window member and the detection window member by a heating module to remove deposit formation of the VOC there from; and controlling the heating module by a control module based on the detection by the temperature detection unit.

18. The method according to claim 17, wherein the heating the source window member and the detection window member by a heating module further comprises:

providing an electrical current to the source window member and the detection window member.

19. The method according to claim 17, wherein the heating the source window member and the detection window member by a heating module further comprises:

providing an electrical current to an electrically conductive source mounting member holding the source window member and an electrically conductive detection mounting member holding the detection window member.

20. The method according to claim 17, wherein the heating the source window member and the detection window member by a heating module further comprises:

providing an electrical current to an electrically conductive source screening member having an amount of transparency to infrared in contact with and covering the source window member and an electrically conductive detection screening member having an amount of transparency to infrared in contact with and covering the detection window member.

* * * * *